United States Patent
Burkhardt et al.

(10) Patent No.: US 8,003,050 B2
(45) Date of Patent: Aug. 23, 2011

(54) DEVICE FOR ANALYZING SAMPLES

(75) Inventors: Claudius Burkhardt, Luzern (CH); Mathias Juch, Baar (CH); Gottlieb Schacher, Kriens (CH); Leo Schwerzmann, Udligenswil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 990 days.

(21) Appl. No.: 11/791,495

(22) PCT Filed: Oct. 25, 2005

(86) PCT No.: PCT/CH2005/000625
§ 371 (c)(1),
(2), (4) Date: May 24, 2007

(87) PCT Pub. No.: WO2006/056083
PCT Pub. Date: Jun. 1, 2006

(65) Prior Publication Data
US 2008/0003137 A1 Jan. 3, 2008

(30) Foreign Application Priority Data
Nov. 25, 2004 (EP) .................... 04027974

(51) Int. Cl.
*G01N 21/00* (2006.01)
*G01N 31/00* (2006.01)
*G01N 33/00* (2006.01)
*G01N 15/06* (2006.01)
*G01N 33/48* (2006.01)
*G01N 27/00* (2006.01)
*G01N 27/30* (2006.01)
*G01N 35/02* (2006.01)

(52) U.S. Cl. ........ 422/64; 422/63; 422/68.1; 422/82.03; 436/47; 436/48

(58) Field of Classification Search .................. None
See application file for complete search history.

(56) References Cited

U.S. PATENT DOCUMENTS
4,066,412 A 1/1978 Johnson et al.
(Continued)

FOREIGN PATENT DOCUMENTS
EP 0 994 355 A1 4/2000
(Continued)

OTHER PUBLICATIONS

D.W. Chan, "Immunoassay Automation, An Updated Guide to Systems", 1996, Academic Press Inc., San Diego, CA, pp. 6-102.
(Continued)

*Primary Examiner* — Jill Warden
*Assistant Examiner* — Charles Hammond
(74) *Attorney, Agent, or Firm* — Dinsmore & Shohl LLP (57) ABSTRACT

A device for analyzing samples is disclosed, which are supplied in sample vessels (2), a central unit (1) with reaction vessels (2), a transport unit (6) for transporting the reaction vessels and at least one analytical unit (7, 8, 9) being provided. The central unit (1) contains a sampling unit (30), by which at least a part of the sample is transferred from the sample vessel (2) to a reaction vessel. At least a part of the reaction vessels is transferred via/by the transport unit (6) to at least one of the analytical units (7, 8, 9). Furthermore, at least one reagent vessel (20, . . . , 23) with at least one reagent is provided, which is supplied to the sample in the reaction vessel for a reaction between the sample and the reagent. Finally, at least one measuring device (5) or at least one measuring unit for the measuring of a physical property of the sample is provided. The device according to the invention works extremely efficiently, simultaneously a minimal effort of resources being required. Thereby, particular advantageous is the modular construction of the device according to the invention, which allows an extension of the analysis capacity as required. Furthermore, the modular construction results in an easier maintenance since defective units (1; 7, 8, 9) can easily be replaced by new ones.

36 Claims, 5 Drawing Sheets

U.S. PATENT DOCUMENTS

| | | | | |
|---|---|---|---|---|
| 4,163,643 | A * | 8/1979 | Hunter et al. | 436/47 |
| 4,528,159 | A | 7/1985 | Liston | |
| 4,536,369 | A | 8/1985 | Sakurada et al. | |
| 4,781,891 | A | 11/1988 | Galle et al. | |
| 4,844,887 | A * | 7/1989 | Galle et al. | 422/65 |
| 4,849,340 | A | 7/1989 | Oberhardt | |
| 5,580,524 | A | 12/1996 | Forrest et al. | |
| 6,290,907 | B1 * | 9/2001 | Takahashi et al. | 422/65 |
| 6,444,171 | B1 * | 9/2002 | Sakazume et al. | 422/65 |
| 6,599,477 | B1 * | 7/2003 | Miyake et al. | 422/64 |
| 6,599,749 | B1 * | 7/2003 | Kodama et al. | 436/47 |
| 6,827,902 | B1 * | 12/2004 | Kuriyama et al. | 422/65 |
| 2002/0106801 | A1 * | 8/2002 | Matsubara et al. | 436/43 |
| 2003/0022380 | A1 * | 1/2003 | Jakubowicz et al. | 436/54 |
| 2005/0013736 | A1 * | 1/2005 | McKeever | 422/63 |

FOREIGN PATENT DOCUMENTS

| | | |
|---|---|---|
| JP | 03-156372 | 7/1991 |
| JP | 06-265559 | 9/1994 |
| JP | 11-133032 | 5/1999 |
| JP | 2002-048800 | 2/2002 |
| JP | 2003-177136 | 6/2003 |
| JP | 2004-09-30 | 9/2004 |
| WO | 02/37078 A2 | 5/2002 |
| WO | 2009 108491 A1 | 9/2009 |

OTHER PUBLICATIONS

Operator's Manual "ACL Advance", Aug. 2000, Instrumentation Laboratory, Boston, MA.

ACL Advance Operation Video Presentation, Instrumentation Laboratory, Boston, MA, pp. 1-4.

"The ACL TOP Hemostasis Testing System: Features and Technical Description", Instrumentation Laboratory, Boston, MA.

Correspondence to Carol Marble from Department of Health & Human Services, dated Jan. 12, 2004, pp. 1-2.

Invoice, Instrumentation Laboratory, dated Feb. 17, 2004, pp. 1-2.

ACL TOP Operator's Manual "Hemostasis", Version 1.1, Oct. 2003, Instrumentation Laboratory, pp. 1-67.

* cited by examiner

DEVICE FOR ANALYZING SAMPLES

FIELD OF THE INVENTION

The present invention relates to a device for analyzing samples.

BACKGROUND AND SUMMARY OF THE INVENTION

Automatic sample analyzing devices are known that are used for quantifying a concentration of a substance dissolved in a liquid sample or for analyzing components of biological liquids, water or the like. Reference is made to the German Patent specification with the publication number DE 198 49 591 C2 describing an automatic analyzing device, in which samples are provided in sample vessels in order that a pipette device can transfer a predetermined sample amount into reaction vessels. Physical properties of the sample are measured by a measuring device in the reaction vessels after reagents have been added. After completion of the measurement, the reaction vessels are cleaned and provided for the next sampling and subsequent measurement. Thereby, the cleaning process proves to be exceedingly lavish and requires a big effort of resources, what is undesired.

Thus, an object of the present invention is to provide a device for analyzing samples, which device does not have the above-mentioned disadvantages.

This object is solved by the features given in the characterizing portion of claim 1. Advantageous embodiments of the invention are specified in further dependent claims.

The invention has the following advantages: By providing a central unit with reaction vessels, a transport unit for transporting the reaction vessels and at least one analytical unit, by further incorporating a sampling unit in the central unit in that at least a part of the sample is transferred from a sample vessel into a reaction vessel, by further transferring at least a part of the reaction vessels into at least one of the analytical units via the transport unit, by providing at least one reagent vessel with at least one reagent that is supplied to the sample in the reaction vessel for a reaction between the sample and the reagent, and, finally, by providing at least one measuring device or at least one measuring unit for measuring a physical property of the sample, an analyzing unit is created which operates extremely efficiently thereby requiring a minimal effort of resources. Thereby, the modular construction of the analyzing unit particularly is advantageous which modular construction allows an extension of the analyzing capacity as it is needed. The modular construction furthermore results in an easier maintenance of the entire analyzing unit since defective units can easily be replaced by new ones.

BRIEF DESCRIPTION OF THE DRAWINGS

In the following, the present invention will be further explained by referring to exemplified embodiments which are represented in drawings. Therein, it is shown in.

DETAILED DESCRIPTION

Figure 1:
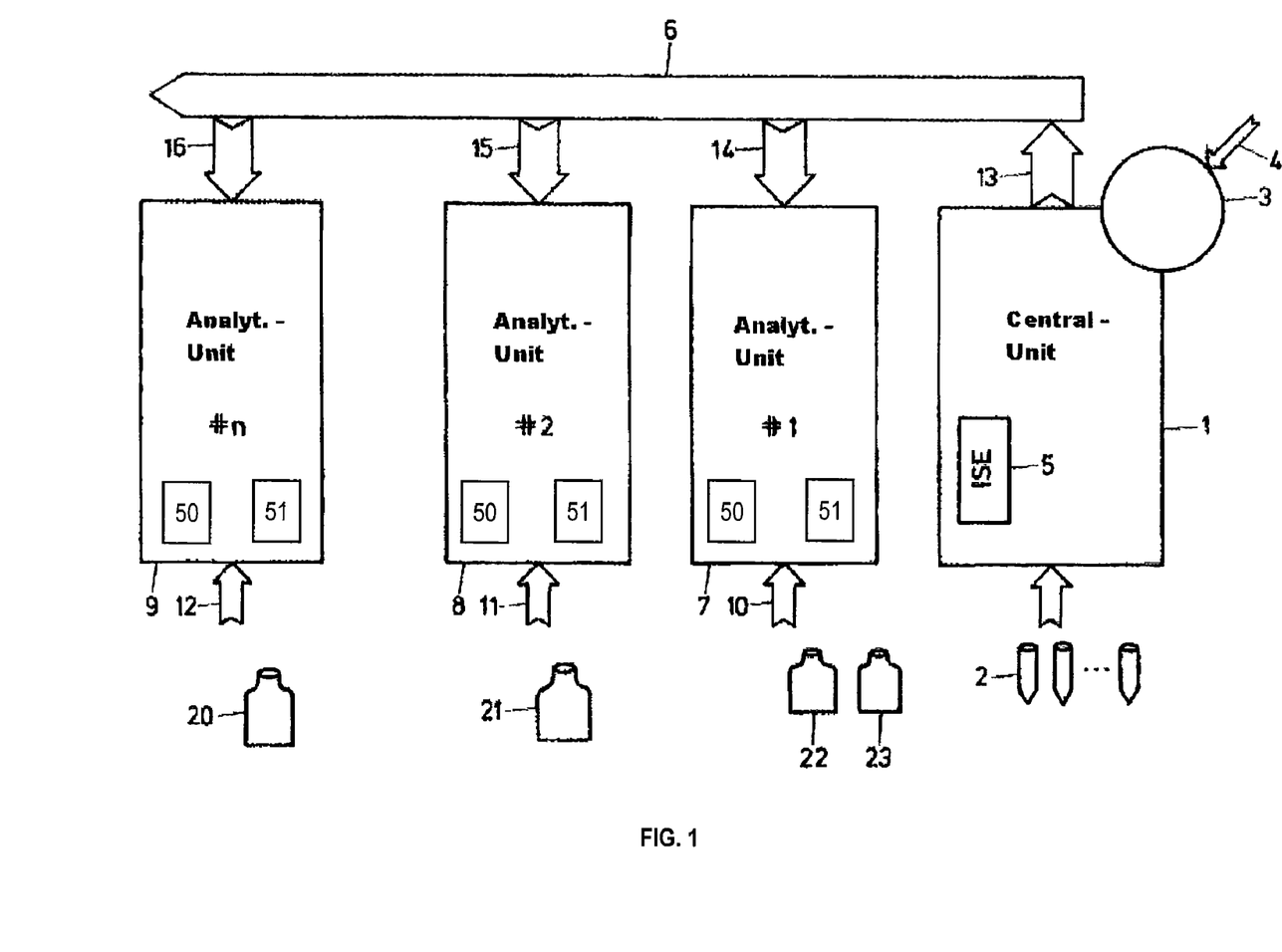
FIG. 1, in a schematically view, a block diagram of the device for analyzing samples according to the present invention.

FIG. 1 shows a simplified block diagram of the device according to the present invention comprising a central unit 1 and several analytical units 7, 8 and 9, which are designated with the consecutive numbers #1, #2, . . . , #n, n indicating an arbitrary integer number of analytical units. Samples to be analyzed are transferred in sample vessels 2 to the central unit 1. Thereby, it is also conceivable that a single sample vessel 2 as well as several sample vessels 2, the latter being preferably arranged in cassettes, is transferred to the central unit 1. In the central unit 1, a predetermined sample amount is taken from the respective sample vessel 2 by means of a sampling unit (not shown in FIG. 1), which is, for example, a pipette device, and filled into a reaction vessel (not shown). The reaction vessels are provided by a separation unit 3, for instance in the form of a shaking funnel, in which orientation and position of the still empty reaction vessels are clearly defined, before filling them with the predetermined sample amount. After the desired amount of a sample, as the case may be by adding water, has been filled into a reaction vessel, it is transferred to a transport unit 6 by means of a supply unit 13. The transport unit 6 is a unidirectional transport unit for the reaction vessels, one or more of the following technologies being used for an implementation:

conveyor belt;
shaking line;
guiding rail with carrier belt.

Depending on the destination of the reaction vessels, they are taken over by the transport unit 6 by means of extraction devices 14 to 16 and are transferred to the respective analytical unit 7, 8 or 9, in which the reaction vessels are prepared for an analysis. The preparation exists, for instance, in that one or more reagents are brought into the respective reaction vessel for triggering a reaction or, to give another example, the sample in the reaction vessel is heated to a predefined temperature. Subsequent to these preparing steps, the physical and/or chemical properties are measured during or after a reaction taking place in the respective reaction vessel, for which one or more measuring units (not shown in FIG. 1) are provided in the analytical unit 7, 8 or 9. With the aid of one or more measuring units, e.g. one ore more of the following properties of the samples, which are present in the reaction vessels, can be determined:

Optical properties, like absorption;
Turbidity (turbidimetry);
Absorption spectra within a defined wave length range;
Secondary fluorescence emission;
Polarization of the fluorescence emission.

As can be further seen in the block diagram schematically represented in FIG. 1, the sample vessels 2 are exclusively transferred to the central unit 1, whereas the reagent vessels 20 to 23 are supplied to the analytical units 7 to 9. This is a consequence of the modular and extensible analyzing device according to the present invention. However, it is explicitly pointed out that embodiments are provided, in which reagents are also required in the central unit 1, for example. It is intended, for example, to perform ion selective measurements (ISE or "Ion Selective Electrode") in a measuring device designated by 5. By these measurements, blood electrolyte concentrations are measured, for example. Hence, the possibility exists that the device according to the invention can be used in ISE-measurements without the need of analytical units. Therefore, the possibility exists that end users who only use the analyzing device for ISE measurements must not purchase any additional modules in form of analytical units but have nevertheless the possibility to extend the analyzing device by incorporating analytical units later.

A control unit (not shown in FIG. 1) is provided e.g. in the central unit 1, or a control unit is connectable to the central unit 1 for the controlling of the device according to the invention. For example, a customary personal computer can be used in the last-mentioned embodiment. The control commands for each of the system components are generated, and feedbacks of the system components are interpreted and evaluated, respectively, in the control unit. Therewith, the position of each of the single reaction vessels and the samples contained therein are also and in particular recorded in the control unit.

In a further embodiment of the device according to the invention, it is intended to provide a label on the reaction vessels for unique identification, which label can be read automatically by an identification unit 50. The identification units are used at necessary positions in the central unit as well as in one or several analytical units. In the control unit, the data read in by the identification units is related to further information—like sample content, administered reagents, measurements to be performed, etc.—in a data bank. For instance, one of the following techniques is suitable for identifying or automatically reading data:

- one- or more dimensional bar code;
- other optical methods;
- transponder;
- marking of molecules in the liquid.

The once used reaction vessels can be used again after a thorough cleaning. However, it has turned out that a one time use of the reaction vessels results in a lower demand for resources (e.g. cleaning agents, water, etc.). Therefore, so-called one way reaction vessels are used in a preferred embodiment of the device according to the invention. Thereby, the construction of the device according to the invention is simplified because no cleaning processes are necessary in the analytical units. The cleaning processes in the central unit are reduced to the cleaning of the sampling unit, by which a particular sample amount is transferred from a sample vessel to a reaction vessel, and, therefore, must be cleaned between the sampling in order to avoid a contamination by transmission from one sample to another. As a result thereof, the analytical units require no cleaning devices, and, in particular, need not to be supplied with water. Thus, only the central unit 1 must be provided with a water connection.

In a further embodiment of the present invention, it is intended that the transport unit 6 transports the reaction vessels not only in one direction but the reaction vessels are transported back to the central unit 1 after completion of an analysis. In such an embodiment, a cleaning station is to be provided instead of the separation unit 3, in which cleaning station the reaction vessels are cleaned and prepared for a new utilization.

Figure 2:
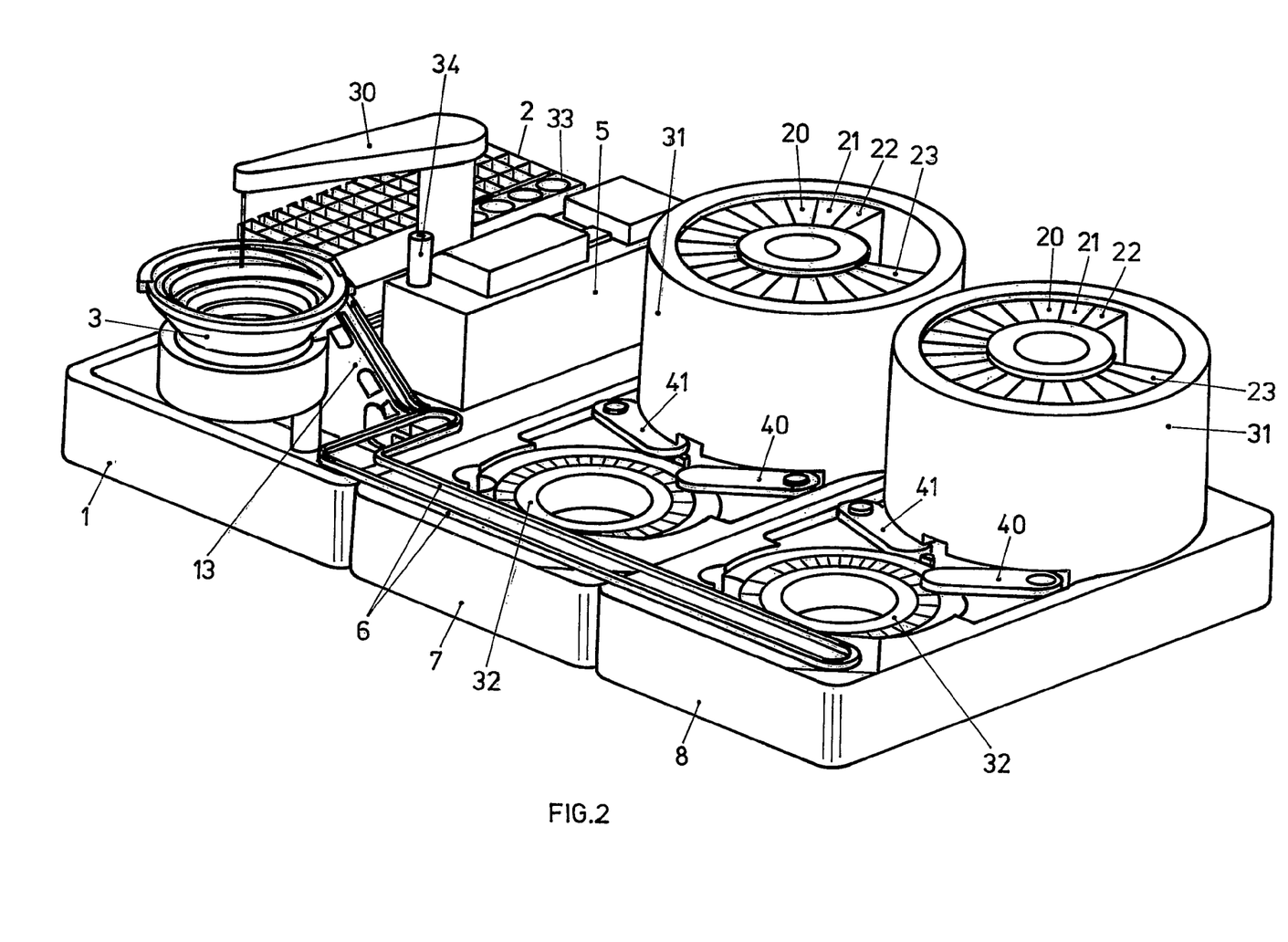
FIG. 2 a first concrete embodiment of the device according to the present invention in a perspective view.

FIG. 2 shows a first concrete embodiment of a device according to the invention. By 1 again a central unit and by 7 and 8 two analytical units are designated. The central unit 1 comprises a separation unit 3 that brings the reaction vessels in a defined position by means of a vibrating shaking funnel. Before the reaction vessels are transferred to the transport unit 6, a defined sample amount is filled in that reaction vessel, which is located in the foremost position, i.e. directly in front of the supply unit 13. Subsequent to the sample transfer, the reaction vessel is transferred to the transport unit 6, and subsequently transferred to one of the analytical units 7 or 8.

The filling of the defined sample amount into the reaction vessel is carried out by means of a sampling unit 30, which is designed as a pipette device and which takes the predefined sample amount from the sample vessels. The sampling unit 30 and the pipette needle, respectively, must be cleaned between each sampling in order that no contamination of the subsequent samples with sample parts from earlier processed samples can occur. For the cleaning, a cleaning unit (not shown in FIG. 2) is provided that is, for example, equipped with several flushing devices for the flushing of the pipette needle. In order that the pipette needle can reach the different positions, the pipette needle is fixed at a swivel arm, which can be swiveled by means of a drive.

Furthermore, the central unit 1 is equipped with a measuring device for the performing of ISE measurements. Thereto, a reaction vessel is not filled with a predetermined sample amount by means of the sampling unit 30 and transferred to the measuring device 5 but the predetermined sample amount is directly supplied to the measuring device 5 by means of the sampling unit 30 via a supply opening 34. According to the need of the measurements performed, the reagents are taken from the reagent vessels 33 and also transferred to the measuring device 5 via the supply opening 34. After completion of the measurements in the measuring device 5, a flushing process is initiated within the measuring device 5 in order that a new measurement can be performed subsequently.

The analytical units 7 and 8 are identically constructed. Besides the transport unit 6 leading through the analytical units 7 and 8, a circular reaction vessel holder 32, which is rotate-able by a rotating drive unit (not shown in FIG. 2), and a likewise circular reagent vessel holder 31, which can also be rotated by a drive unit, are provided. Two transfer units 40, 41 are provided to position a reaction vessel underneath a corresponding reagent vessel in order that an intended amount of reagent can be administered into the reaction vessel from the reagent vessel. In a further embodiment of the mentioned kind, the transfer units 40, 41 are additionally used as mixers to mix the samples with the supplied reagents.

Embodiments are also conceivable, in which only one transfer unit or in which more than two transfer units to position the reaction vessels are provided. Moreover, embodiments are also conceivable, in which reagent vessels instead of the reaction vessels are being positioned by transfer units, or the reaction vessels as well as the reagent vessels are being positioned.

The reagent vessels 20 to 23 have a circle segment-like cross section for optimal exploitation of the circular reagent vessel holder 31 and are designed as a self dispending means with a nozzle on the bottom side for the dispensing of a exactly dose-able amount of reagents. The self dispensing means as well as the reagent vessel can be realized, for example, according to the manner described in the international application with the application number PCT/CH 2004/000316. Therefore, its content is herewith incorporated by reference in its entirety.

It is explicitly pointed out that the self dispensing means can be used in all described embodiments in the foregoing mentioned sense.

Figure 3:
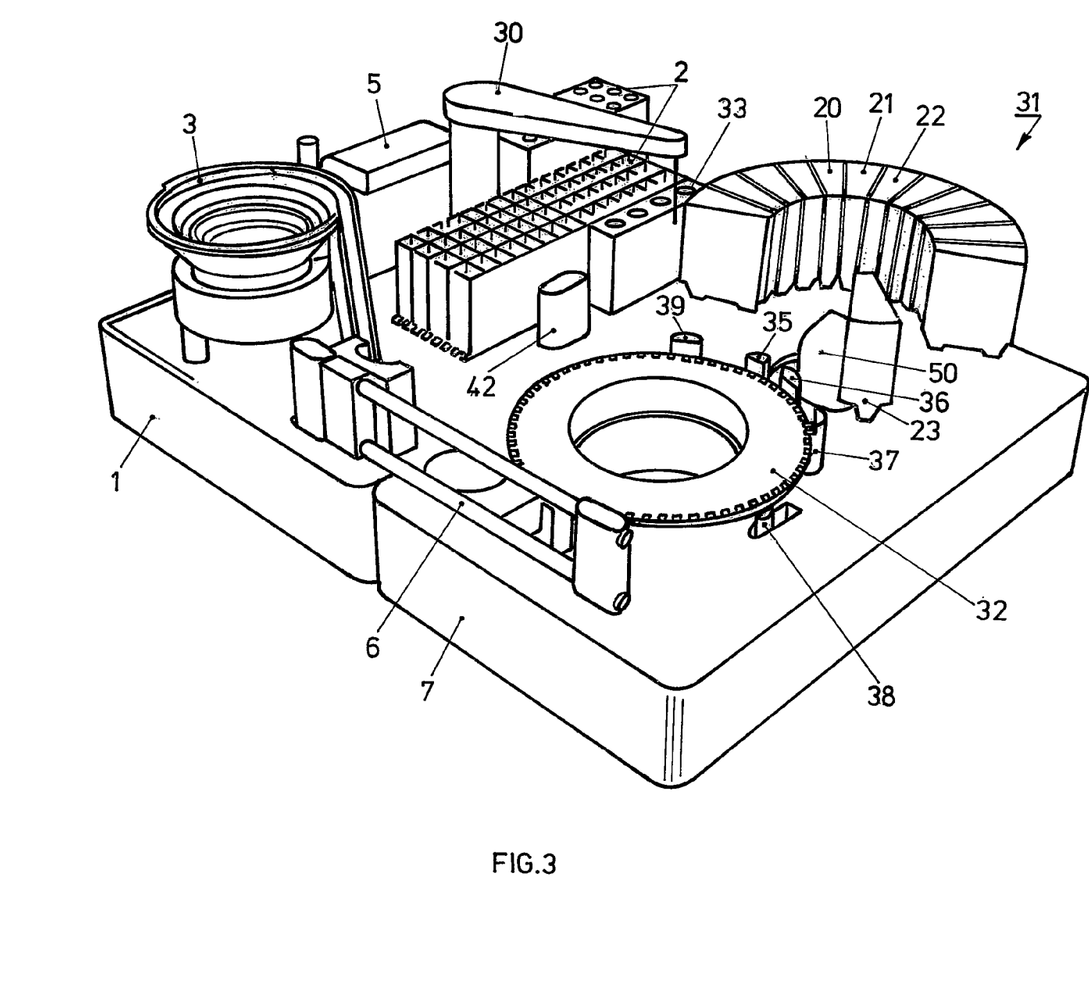
FIG. 3 a second concrete embodiment of the device according to the present invention in a perspective view.

FIG. 3 shows a second concrete embodiment of the device according to the invention. In contrast to the embodiment according to FIG. 2, the embodiment according to FIG. 3 consists of a central unit 1 and a single analytical unit 7. Furthermore, the circumferences of both holders 31 and 32, which are only represented partly, overlap each other such that reagents from one of the reagent vessels can be given into a reaction vessel. Therefore, the reagent vessel holder 31 is arranged above the reaction vessel holder 32.

The central unit 1 substantially consists of the same components as the central unit according to FIG. 2. The two embodiments only differ from another by the different arrangement of the components and the now apparent cleaning unit 42, in which the pipette needle of the sampling unit 30 can be cleaned. The cleaning unit 42 is provided adjacent to one side of the analytical unit 7 in the central unit 1, and the measuring device 5 is arranged on the opposite side, whereas this is not mandatory. Furthermore, a reagent vessel holder is designated by 33, in which the reagents required in the measuring unit 5 are contained. The sampling unit 30, which is still centrally arranged in the central unit 1 with swiveling arm and drive unit 4 driving the swiveling arm, has good access to the samples in the sample vessels, to the reaction vessels coming from the separation unit 3 as well as to the cleaning unit 42.

According to FIG. 3, the samples can be transferred to the central unit 1 in two differently sized sample holders. Therewith, sample holders having five and fifteen samples can be transferred to the central unit 1.

The analytical unit 7 has again a circular reaction vessel holder 32 and a reagent vessel holder 31 overlapping the reaction vessel holder 32, in which reagent vessel holder 31 the circle-segment-shaped reagent vessels 20 to 22 are hold, the reagent vessel holder 31 and the associated reaction vessels not being represented in FIG. 2 within the overlapping area of the holders 31 and 32, so that the further units lying in the overlapping area can be seen. The further units are at first mixing units 35 and 36, a reading unit 50, which is used for instance for the reading of a bar code on a reagent vessel or a reaction vessel, and measuring units 36 to 39. The last mentioned can also be arranged outside the overlapping area. The mixing units 35 and 36 are used for mixing the samples in the reaction vessels, the mixing units 35 and 36 being particularly activated after adding a reagent. Furthermore, the mixing units 35 and 36 are preferably used before a measuring takes place in one of the measurement units 36 to 39.

Figure 4:
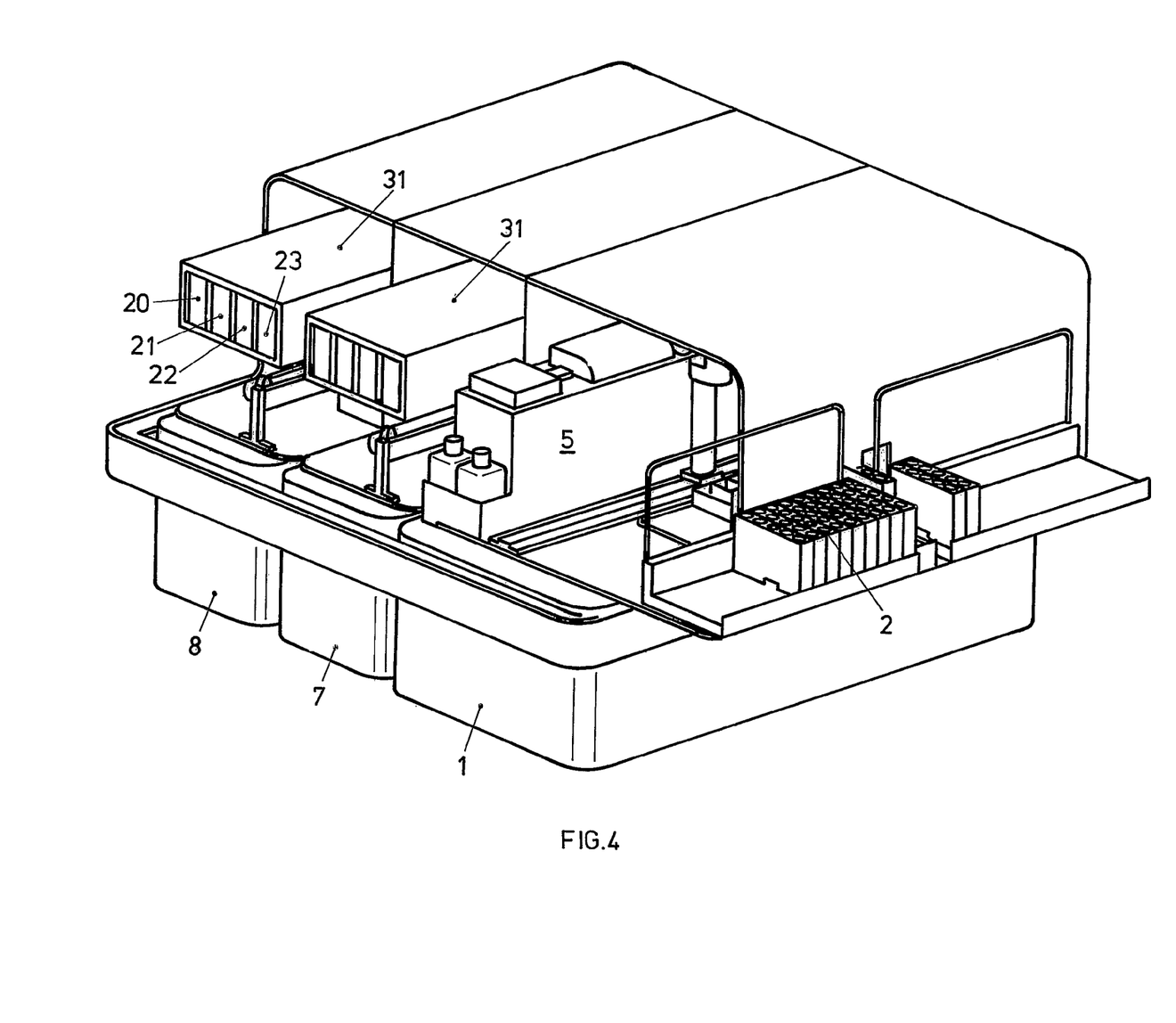
FIG. 4 a third concrete embodiment of the device according to the present invention in a perspective view.

FIG. 4 shows a third concrete embodiment of the device according to the invention that is again represented in a perspective view with a cover partially cut open. A central unit 1 in combination with two analytical units 7 and 8 are visible. The sample vessels are supplied to the central unit 1 in cassettes, five sample vessels being contained in each cassette. The cassettes are inserted into the central unit 1 on one side. For sampling, again a sampling unit (not shown in FIG. 4) is included, which transfers the predefined sample amount either into the measuring device or into a reaction vessel.

The analytical units 7 and 8 are, in contrast to those in the embodiments according to FIGS. 2 and 3, not equipped with a circular but with a stationary rectangular reagent vessel holder 31. In case a reagent must be administered into a reaction vessel, it is brought under the nozzle of the corresponding reagent vessel by a Φ-R-positioning unit. Thereafter, the reaction vessel is guided, if necessary, to a measuring unit in the same manner.

Figure 5:
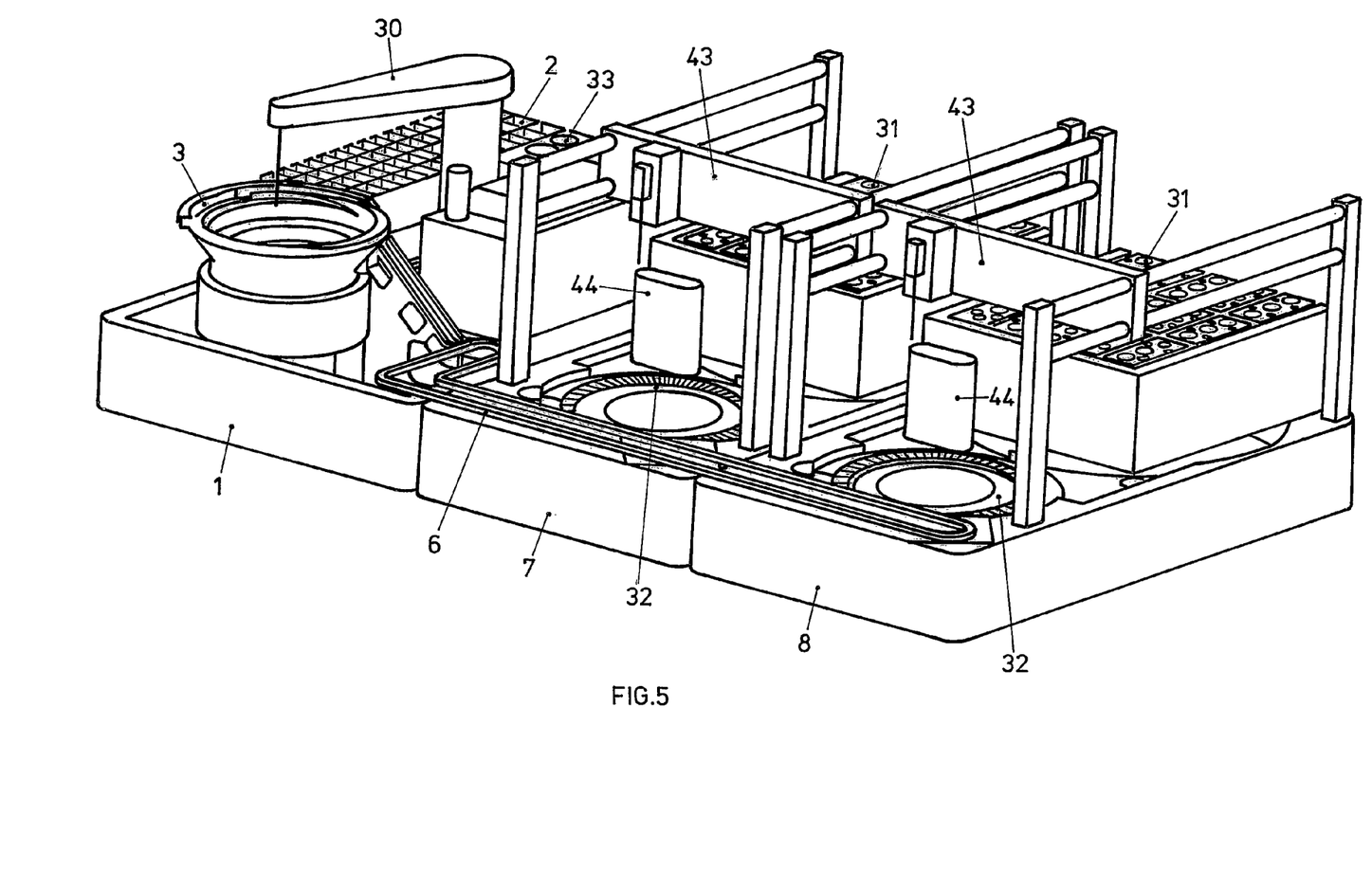
FIG. 5 a fourth concrete embodiment of the device according to the present invention in a perspective view.

Finally, FIG. 5 shows a fourth embodiment of the device according to the invention, again in perspective view. From FIG. 5, it can be clearly seen that the analytical units 7, 8 now comprise a pipette device 43, by means of which the reagents are supplied to the reaction vessels, which are contained in a circular reaction vessel holder 32. The pipette device 43 is thereby realized as X-Y positioning unit, which takes a required reagent from a reagent vessel and administers it in a reaction vessel. The pipette needle must be cleaned between each pipette processes in order that a reagent is not contaminated by another reagent, which still adheres at the pipette needle from the previous pipette process. For this reason, a needle cleaning unit 44 is provided, by which the pipette needle is cleaned between the pipette processes.

For all described embodiments of the device according to the invention, it is conceivable that temperature adjustment units 51 are provided in the analytical units in order to set the temperature of the reagents in the reagent vessels and/or the temperature of the samples in the reaction vessels to predefined values. Therefore, the reagent vessel holders and/or the reaction vessel holders are enclosed to a large extend such that heat inflows or heat outflows are prevented as much as possible. Therefore, the temperature adjustment unit 51, for example, only acts on the reagent vessels while a further temperature adjustment unit only acts on the reaction vessels, the reagent vessels being kept, for example, at a temperature of approx. 10° Celsius and the reaction vessels being kept, for example, at a temperature of approx. 37° Celsius.

In the same manner, so-called sample pre-treatment units can be comprised in at least one or in all analytical units described along the above-mentioned embodiments, in which sample pre-treatment units, for example, the separation of a cellular part of the sample or an extraction, a separation and/or a purification of certain sample constituents is performed. Such sample pre-treatments are necessary for example in immunological, molecular or clinical-chemical analysis. The sample pre-treatment unit is preferably directly arranged at the transfer position of a reaction vessel to an analytical unit.

The invention claimed is:

1. A device for analyzing samples administered from a plurality of sample vessels, said device comprising:
    a central unit having a supply of reaction vessels and a sampling unit by which at least a part of a sample is transferred from one of the plurality of sample vessels into a reaction vessel supplied from the supply of reaction vessels;
    at least one analytical unit having a plurality of self dispensing reagent vessels provided in a cassette;
    a transport unit which transports at least a part of the reaction vessels from the central unit to the at least one analytical unit such that the analytical unit supplies a reagent directly from at least one of the plurality of self dispensing reagent vessels provided in the cassette into the supplied reaction vessel for triggering a reaction between the sample and the supplied reagent;
    a supply unit configured to provide the supplied reaction vessel, while holding the sample therein, from the central unit to the transport unit;
    an extraction device configured to remove the supplied reaction vessel from the transport unit and provide the supplied reaction vessel, while holding the sample therein, to the at least one analytical unit;
    at least one measuring unit provided in the at least one analytical unit and which measures a physical property of the sample held in the supplied reaction vessel; and
    a measuring device included in the central unit, and wherein the sample is introduced directly into the measuring device from the sample vessel via the sampling unit of the central unit.

2. The device according to claim 1, wherein the measuring device included in the central unit performs an ion-selective-electrolyte measurement, and wherein the central unit has a reagent supply, and the sample and a reagent from the reagent supply are introduced into the measuring device via the sampling unit of the central unit.

3. The device according to claim 1, wherein the transport unit is selected from a conveyor belt, a shaking line, and a guiding rail with a carrier belt.

4. The device according to claim 1, wherein the reaction vessels are disposable.

5. The device according to claim 1, wherein the transport unit transports the supplied reaction vessel only in one direction, namely from the central unit to one of the at least one analytical units.

6. The device according to claim 1, wherein a separation unit is provided in the central unit to supply the reaction vessels.

7. The device according to claim 6, wherein the separation unit is a vibrating shaking funnel.

8. The device according to claim 1, further comprising an identification unit configured to identify the supplied reaction vessel and the supplied reagent.

9. The device according to claim 8, wherein the identification unit uses one or more of the following technologies bar codes, other optical methods, transponder, and marking molecules.

10. The device according to claim 1, further comprising an identification unit provided in the analytical unit and configured to identify the supplied reaction vessel and the supplied reagent.

11. The device according to claim 1, wherein the analytical unit has a temperature adjustment unit configured to adjust temperature of the supplied reagent.

12. The device according to claim 1, wherein the analytical unit has a temperature adjustment unit which is configured to adjust temperature of the sample contained in the supplied reaction vessel.

13. The device according to claim 1, wherein said measuring unit is configured to determine one or more of the following physical properties of the sample: optical properties, turbidity, absorption spectra, secondary fluorescence emission, and polarization.

14. The device according to claim 1, wherein the at least one analytical unit has a mixing unit configured to mix the sample with the supplied reagent.

15. The device according to claim 1, wherein the central unit further comprises a cleaning unit configured to clean the sampling unit, said cleaning unit being provided with a supply of water.

16. The device according to claim 1, wherein the sampling unit is a pipette unit provided on a swivel arm.

17. The device according to claim 1, wherein the cassette is circular in shape.

18. The device according to claim 1, wherein the cassette is rectangular in shape.

19. The device according to claim 1, wherein the cassette is configured as a circular reagent vessel holder, and the at least one analytical unit further comprises a circular reaction vessel holder configured to hold a plurality of supplied reaction vessels provided by the extraction device, wherein the circular reaction vessel holder is overlapped partially by the circular reagent vessel holder such that the reagent may by dispensed from the at least one of the plurality of self dispensing reagent vessels provided in the cassette directly into the supplied reaction vessel held by the circular reaction vessel holder, and wherein both the reagent vessel holder and the reaction vessel holder are configured to rotate via a drive unit.

20. The device according to claim 1, wherein the at least one analytical unit further comprises a reaction vessel holder configured to hold a plurality of supplied reaction vessels provided by the extraction device, and a pair of transfer units configured to position the supplied reaction vessel such that the reagent may by dispensed from the at least one of the plurality of self dispensing reagent vessels provided in the cassette directly into the supplied reaction vessel.

21. The device according to claim 1, wherein the at least one analytical unit further comprises a reaction vessel holder configured to hold a plurality of supplied reaction vessels provided by the extraction device, and a pair of transfer units configured to position the supplied reaction vessel such that the reagent may by dispensed from the at least one of the plurality of self dispensing reagent vessels provided in the cassette directly into the supplied reaction vessel and to mix the sample in the supplied reaction vessel with the reagent.

22. A modular device for analyzing samples, which are administered into sample vessels, comprising:
a transport unit for transporting reaction vessels;
at least one analytical unit;
a central unit with the reaction vessels and which includes a sampling unit, by which at least a part of the sample is transferred from a sample vessel into a reaction vessel, that at least a part of the reaction vessels is transferable to the at least one analytical unit via the transport unit, that at least one reagent vessel with at least one reagent is provided in the at least one analytical unit, in which the reagent is supplied directly from the reagent vessel to the sample in the reaction vessel for a reaction between the sample and the reagent;
at least one measuring unit which measures a physical property of the sample provided in the analytical unit; and
a measuring device included in the central unit, and wherein the sample is introduced directly into the measuring device from the sample vessel via the sampling unit of the central unit.

23. The device according to claim 22, wherein the measuring device performs an ion-selective-electrolyte measurement and required reagents for the ion-selective-electrolyte measurement are provided in the central unit.

24. The device according to claim 22, wherein the at least one reagent is provided in single reagent vessels, or in a reagent vessel holder with the at least one reagent vessel.

25. The device according to claim 24, wherein a self dispensing means is provided for each reagent vessel.

26. The device according to claim 22, wherein the transport unit transports the reaction vessels only in one direction from the central unit to the at least one analytical unit.

27. The device according to claim 22, wherein a separation unit is provided in the central unit, and wherein the reaction vessels are provided in the separation unit.

28. The device according to claim 22, wherein one or more of the reaction vessels and the at least one reagent vessel is identifiable by at least one of dimensional bar codes, optical methods, a transponder, and marking molecules.

29. The device according to claim 22, wherein identification units for identification of one or more of the reaction vessels and the at least one reagent vessel are provided in the at least one analytical unit.

30. The device according to claim 22, wherein the at least one analytical unit has temperature adjustment units which adjust a temperature of the at least one reagent.

31. The device according to claim 22, wherein the at least one analytical unit has temperature adjustment units which adjust a temperature of the samples contained in the reaction vessels.

32. The device according to claim 22, wherein only the central unit is supplied with water.

33. The device according to claim 22, wherein the at least one analytical unit has a mixing unit which mixes the sample with administered one of the at least one reagent.

34. The device according to claim 22, wherein a cleaning unit which cleans the sampling unit is provided in the central unit.

35. The device according to claim 22, wherein the sampling unit is a pipette unit.

36. The device according to claim 22, wherein a sample pre-treatment unit is included in one or more of the central unit and the at least one analytical unit.

* * * * *

UNITED STATES PATENT AND TRADEMARK OFFICE
CERTIFICATE OF CORRECTION

PATENT NO. : 8,003,050 B2
APPLICATION NO. : 11/791495
DATED : August 23, 2011
INVENTOR(S) : Burkhardt et al.

It is certified that error appears in the above-identified patent and that said Letters Patent is hereby corrected as shown below:

Title Page, Item (30)
Foreign Application Priority Data
"(EP...............04027974" should read --(EP............... 004027974.7--

Col. 8, Claim 21, Line 6, "may by" should read --may be--

Signed and Sealed this
Seventh Day of February, 2012

David J. Kappos
*Director of the United States Patent and Trademark Office*